US010022380B2

(12) United States Patent
Linder et al.

(10) Patent No.: US 10,022,380 B2
(45) Date of Patent: Jul. 17, 2018

(54) TREATMENT OF SOLID TUMOURS

(71) Applicant: Vivolux AB, Uppsala (SE)

(72) Inventors: Stig Linder, Bromma (SE); Mårten Fryknäs, Knivsta (SE); Rolf Larsson, Uppsala (SE)

(73) Assignee: VIVOLUX AB, Uppsala (SE)

( * ) Notice: Subject to any disclaimer, the term of this patent is extended or adjusted under 35 U.S.C. 154(b) by 0 days.

(21) Appl. No.: 15/625,337

(22) Filed: Jun. 16, 2017

(65) Prior Publication Data

US 2017/0348317 A1 Dec. 7, 2017

Related U.S. Application Data

(62) Division of application No. 14/006,277, filed as application No. PCT/SE2012/000034 on Mar. 14, 2012.

(51) Int. Cl.
| | |
|---|---|
| A61K 31/53 | (2006.01) |
| A61K 31/4706 | (2006.01) |
| C07D 487/04 | (2006.01) |
| A61K 31/4412 | (2006.01) |
| A61K 45/06 | (2006.01) |
| A61K 31/16 | (2006.01) |
| A61K 31/4196 | (2006.01) |
| A61K 31/4422 | (2006.01) |
| A61K 31/70 | (2006.01) |
| A61K 31/365 | (2006.01) |

(52) U.S. Cl.
CPC ............. *A61K 31/53* (2013.01); *A61K 31/16* (2013.01); *A61K 31/365* (2013.01); *A61K 31/4196* (2013.01); *A61K 31/4412* (2013.01); *A61K 31/4422* (2013.01); *A61K 31/4706* (2013.01); *A61K 31/70* (2013.01); *A61K 45/06* (2013.01); *C07D 487/04* (2013.01); *A61K 2300/00* (2013.01)

(58) Field of Classification Search
CPC ............................ A61K 31/53; A61K 31/4706
See application file for complete search history.

(56) References Cited

U.S. PATENT DOCUMENTS

| 4,831,038 | A | 5/1989 | Trouet et al. |
| 5,480,906 | A | 1/1996 | Creemer et al. |
| 9,562,046 | B2 | 2/2017 | Linder |
| 2003/0092716 | A1 | 5/2003 | Almstead et al. |
| 2012/0095045 | A1 | 4/2012 | Yeo |

FOREIGN PATENT DOCUMENTS

| WO | 99/02143 | A2 | 1/1999 |
| WO | 02/089809 | A1 | 11/2002 |
| WO | 2006/055412 | A1 | 5/2006 |
| WO | 2006/113703 | A2 | 10/2006 |
| WO | 2007/128820 | A1 | 11/2007 |
| WO | 2009/035534 | A2 | 3/2009 |
| WO | 2010/151005 | A2 | 12/2010 |

OTHER PUBLICATIONS

Levine, Autophagy and Cancer, Nature, 446:745-747, Apr. 12, 2007.
Tannock et al, Limited Penetration of Anticancer Drugs through Tumor Tissue: A Potential Cause of Resistance of Solid Tumors to Chemotherapy, Clinical Cancer Research, vol. 8, 878-884, Mar. 2002.
Mueller-Klieser, Multicellular spheroids, A review on cellular aggregates in cancer research, Cancer Research Clinical Oncology (1987) 113: 101-122.
Smalley et al, Life Isn't Flat: Taking Cancer Biology to the Next Dimension, In Vitro Cell. Dev. Biol.—Animal 42:242-247, Sep. and Oct. 2006.
Frankel et al, Abrogation of Taxol-induced G2-M Arrest and Apoptosis in Human Ovarian Cancer Cells Grown as Multicellular Tumor Spheroids, Cancer Research 1997: 57: 2388-2393.
Karantza-Wadsworth et al, Autophagy mitigates metabolic stress and genome damage in mammary tumorigenesis, Genes & Development 2007 21: 1621-1635.
Mizushima et al, Autophagy fights disease through cellular self-digestion, Nature, 451:1069-1075, Feb. 28, 2008.
Degenhardt et al, Autophagy promotes tumor cell survival and restricts necrosis, inflammation, and tumorigenesis, Cancer Cell 10, 51-64, Jul. 2006.
Zietarska et al, Molecular Description of a 3D In Vitro Model for the Study of Epithelial Ovarian Cancer (EOC), Molecular Carcinogenesis, 46: 872-885 (2007).
Lamb et al, The Connectivity Map: Using Gene-Expression Signatures to Connect Small Molecules, Genes, and Disease, Science Magazine, 313:1929-1935, Sep. 29, 2006.
Schmidt-Mende et al, Early mitochondrial alterations in ATRA-induced cell death, Cell Death and Differentiation (2006) 13, 119-128.
Yu et al, Chelators at the Cancer Coalface: Desferrioxamine to Triapine and Beyond, Clinical Cancer Research 2006; 12(23):6876-6883, Dec. 1, 2006.
Amaravadi et al, The Roles of Therapy-Induced Autophagy and Necrosis in Cancer Treatment, Clinical Cancer Research 2007, 13(24):7271-7279, Dec. 15, 2007.
Klionsky et al, Guidelines for the use and interpretation of assays for monitoring autophagy in higher eukaryotes, Autophagy, Feb. 16, 2008; 4(2): 151-175.

(Continued)

*Primary Examiner* — Samira Jean-Louis
(74) *Attorney, Agent, or Firm* — Porter Wright Morris & Arthur LLP

(57) ABSTRACT

A cell permeable iron chelator, optionally in combination with an autophagy inhibiting agent, is used for treating a solid cancer tumor in a person. A preferred chelator is an alkyl substituted N-(1-pyridine-2-yl-methylidene)-N-(9H-1, 3,4,9-tetraaza-fluoren-2-yl)-hydrazine. A preferred autophagy inhibiting agent is chloroquine. Also disclosed is a pharmaceutical composition comprising iron chelator, pharmaceutically acceptable carrier and, optionally, autophagy inhibiting agent; and a method of treating cancer by administering cancer combating-effective amount(s) of the iron chelator or the combination of iron chelator and autophagy inhibiting agent.

16 Claims, 11 Drawing Sheets

(56) References Cited

OTHER PUBLICATIONS

Figure 1:
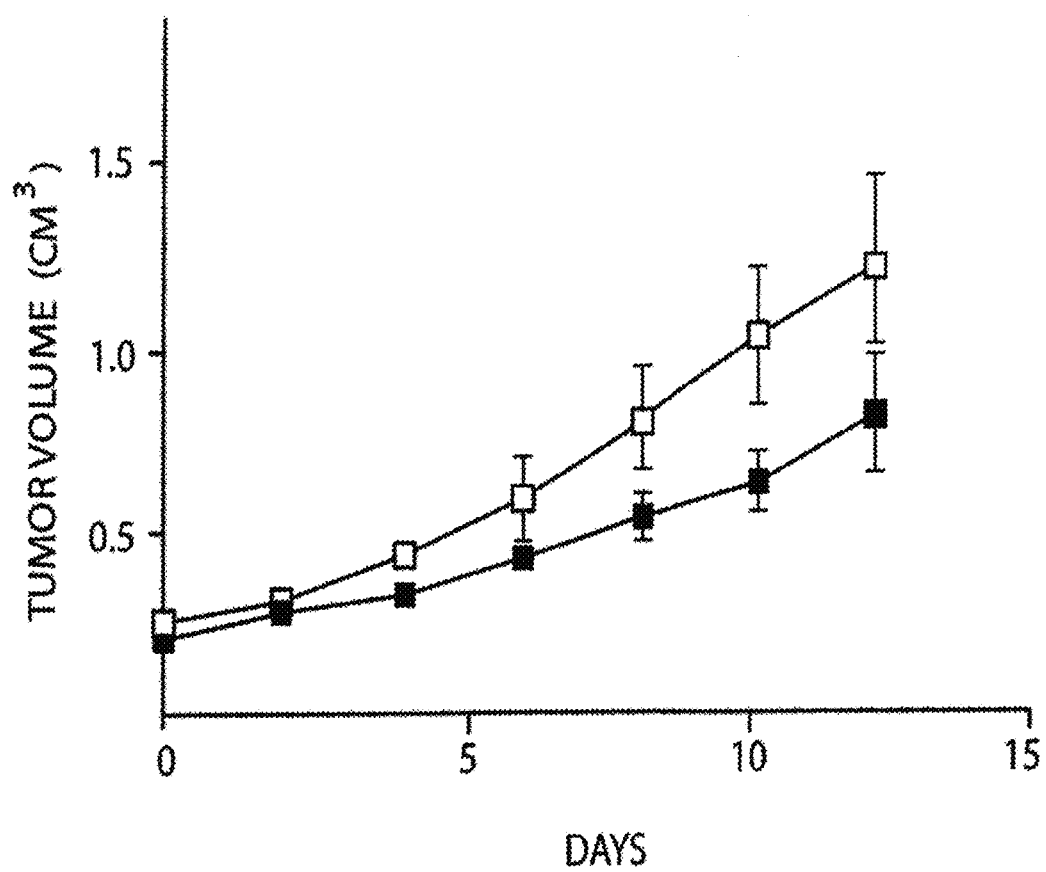

Edinger et al, Death by design: apoptosis, necrosis and autophagy, Current Opinion in Cell Biology, 2004, 16:663-669.

Linden et al, The antimycotic ciclopirox olamine induces HIF-1 alpa stability, VEGF expression, and angiogenesis, The FASEB Journal, 10.1096/fj.0586fje. Published online Feb. 19, 2003 (20 pages).

Hägg et al, A novel high-through-put assay for screening of pro-apoptotic drugs, Investigational New Drugs 20; 253-259, 2002.

Friedrich et al, A Reliable Tool to Determine Cell Viability in Complex 3-D Culture: The Acid Phosphatase Assay, J Biomol Screen, 2007, 12: 925-937.

Herrmann et al, Screening for Compounds That Induce Apoptosis of Cancer Cells Grown as Multicellular Spheroids, Journal of Biomolecular Screening 13(1):1-8; 2008.

Carracedo et al, The PTEN-PI3K pathway: of feedbacks and cross-talks, Oncogene (2008), 27:5527-5541.

Bruick, Expression of a gene encoding the proapoptotic Nip3 protein is induced by hypoxia, PNAS, vol. 97, No. 16, 9082-9087, Aug. 1, 2000.

Tong et al, Metabolic regulation of citrate and iron by aconitases: role of iron-sulfur cluster biogenesis, Biometals (2007) 20: 549-564.

Lum et al, Growth Factor Regulation of Autophagy and Cell Survival in the Absence of Apoptosis, Cell, vol. 120, 237-248, Jan. 28, 2005.

Mazure, Hypoxia-induced autophagy: cell death or cell survival?, Current Opinion in Cell Biology, 2009, 22: 1-4.

Arteel et al, Reductive metabolism of the hypoxia marker pimonidazole is regulated by oxygen tension independent of the pyridine nucleotide redox state, Eur. J. Biochem. 253, 743-750 (1998).

Corradetti et al, Regulation of the TSC pathway by LKB1: evidence of a molecular link between tuberous sclerosis complex and Peutz-Jeghers syndrome, Genes Dev. 2004 18: 1533-1538.

Schieke et al, The Mammalian Target of Rapamycin (mTOR) Pathway Regulates Mitochondrial Oxygen Consumption and Oxidative Capacity, The Journal of Biological Chemistry, vol. 281, No. 37, pp. 27643-27652, Sep. 15, 2006.

Velde et al, BNIP3 and Genetic Control of Necrosis-Like Cell Death through the Mitochondrial Permeability Transition Pore, Molecular and Cellular Biology, Aug. 2000, vol. 20, No. 15, p. 5454-5468.

Cunningham et al, mTOR controls mitochondrial oxidative function through a YY1-PGC-1 alpha transcriptional complex, Nature, 450:736-741, Nov. 29, 2007.

Ramanathan et al, Direct control of mitochnodrial function by mTOR, PNAS, Dec. 29, 2009, vol. 106, No. 52, 22229-22232.

Torti et al, Tumor Cell Cytotoxicity of a Novel Metal Chelator, Blood, vol. 92, No. 4, pp. 1384-1389 (1998).

Rakba et al, Antiproliferative and apoptotic effects of O-Trensox, a new synthetic iron chelator, on differentiated human hepatoma cell lines, Carcinogenesis, vol. 21, No. 5, pp. 943-951, 2000.

Richardson, Iron chelators as therapeutic agents for the treatment of cancer, Critical Reviews in Oncology/Hematology 42 (2002) 267-281.

Wang et al, Dexamethasone Represses Signaling through the Mammalian Target of Rapamycin in Muscle Cells by Enhancing Expression of REDD1, The Journal of Biological Chemistry, vol. 281, No. 51, pp. 39128-39134, 2006.

Tracy et al, BNIP3 Is an RB/E2F Target Gene Required for Hypoxia-Induced Autophagy, Molecular and Cellular Biology, Sep. 2007, vol. 27, No. 17, p. 6229-6242.

Finch et al, Triapine (3-Aminopyridine-2-carboxaldehyde-thiosemicarbazone): A Potent Inhibitor of Ribonucleotide Reductase Activity with Broad Spectrum Antitumor Activity, Biochemical Pharmacology, vol. 59, pp. 983-991, 2000.

Sariban-Sohraby et al, Comparison of Energy Metabolism in Human Normal and Neoplastic (Burkitt's Lymphoma) Lymphoid Cells, Cancer Research 43, 4662-4664, Oct. 1983.

Ohyashiki et al, The oral iron chelator deferasirox represses signaling through the mTOR in myeloid leukemia cells by enhancing expression of REDD1, Cancer Sci, May 2009, vol. 100, No. 5, p. 970-977 (online Mar. 9, 2009).

Degtyarev et al, Akt inhibition promotes autophagy and sensitizes PTEN-null tumors to lysosomotropic agents, J. Cell. Biol., vol. 183, No. 1, p. 101-116 (2008).

Bredel-Geissler et al, Proliferation-Associated Oxygen Consumption and Morphology of Tumor Cells in Monolayer and Spheroid Culture, Journal of Cellular Physiology, 153:44-52 (1992).

Eshba et al, Synthesis of Some Substituted-1,2,4-triazino[5,6-b]indole Derivatives as Potential Antiviral and Anticancer Agents, PPharmazie, 42(10): 664-666 (1987).

Freyer et al, In Situ Oxygen Consumption Rates of Cells in V-79 Multicellular Spheroids During Growth, Journal of Cellular Physiology, 118: 53-61 (1984).

Kunz et al, "Oncogene-Associated Growth Behavior and Oxygenation of Multicellular Spheroids from Rat Embryo Fibroblasts", Oxygen Transport to Tissue XV, P. Vaupel, Editor, Plenum Press, New York, pp. 359-366, (1994).

Sasaki, Chloroquine Potentiates the anti-cancer effect of 5-fluorouracil on colon cancer cells, BMC Cancer 2010, 10:370 (11 pages).

Sutherland et al, Radiation Response of Multicell Spheroids an In Vitro Tumour Model, Current Topics in Radiation Research Quarterly, 11: 87-139 (1976).

Sasaki et al., Chloroquine potentiates the anti-cancer effect of 5-flurouracil on colon cancer cells, BMC Cancer, 10:370, p. 1471-2407 (Jul. 15, 2010).

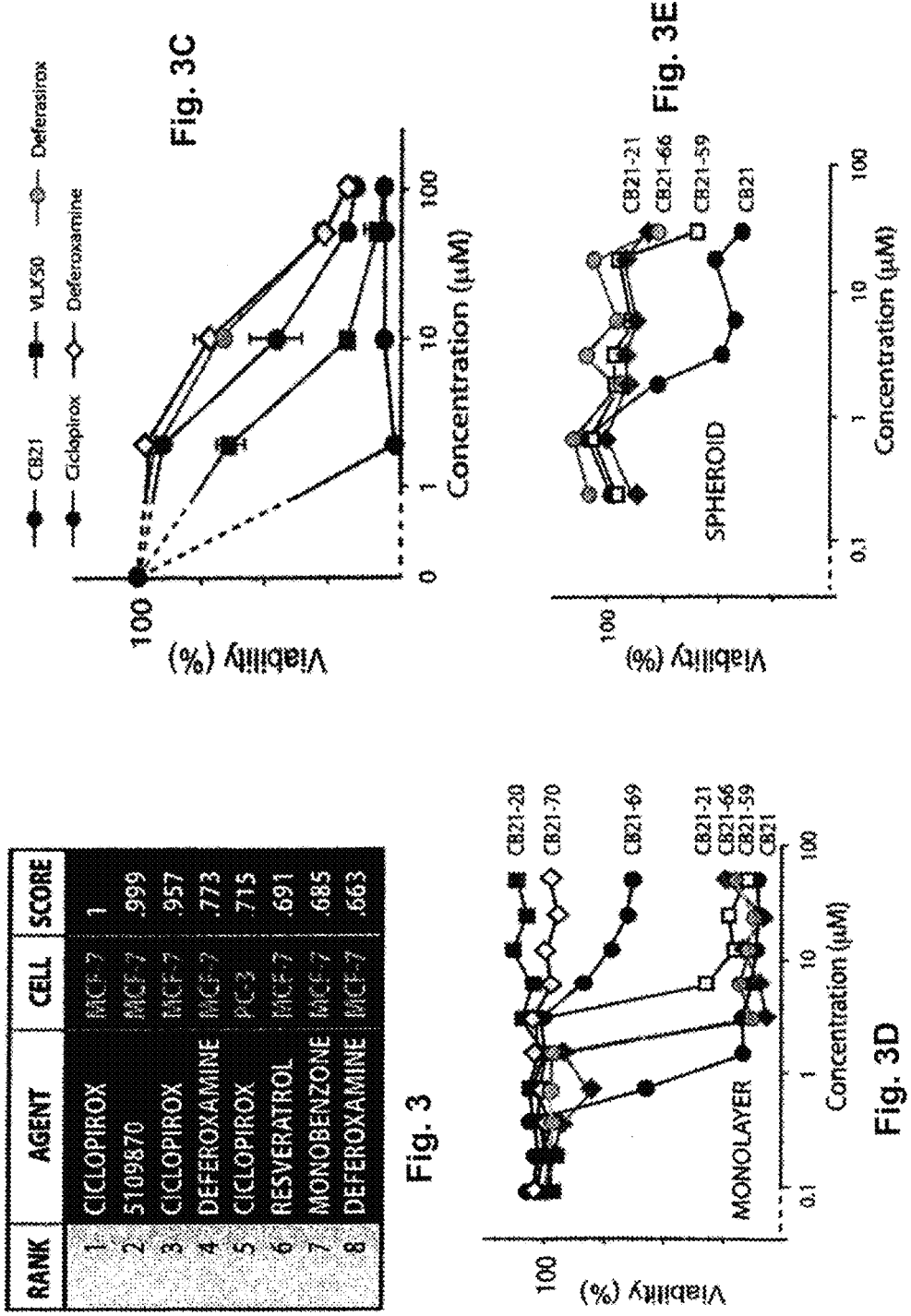

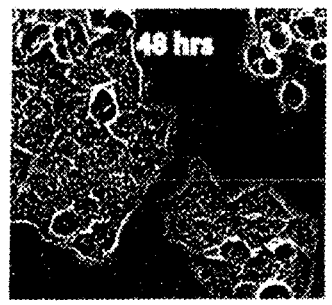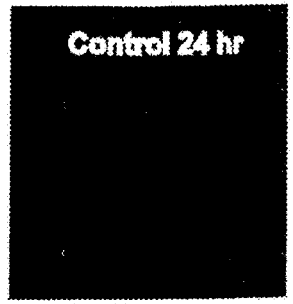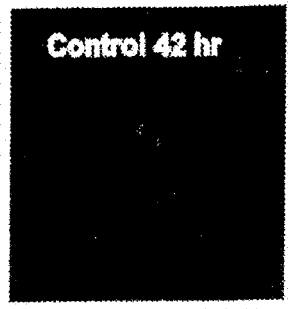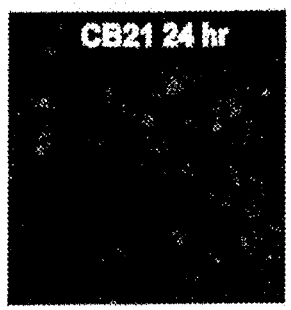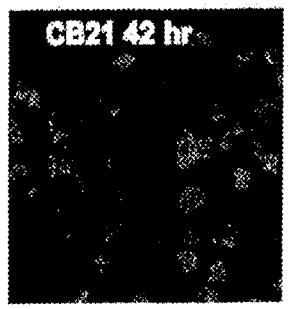
Fig. 4A          Fig. 4B
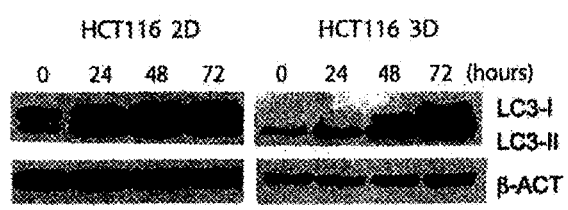
Fig. 4C
Fig. 4D
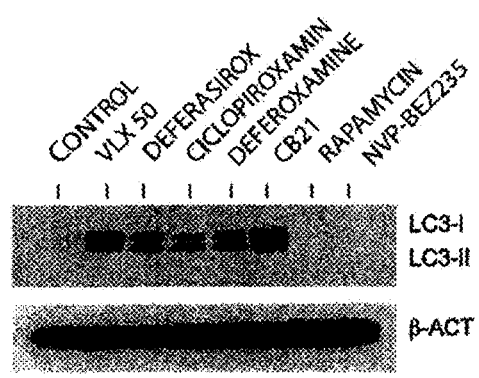
Fig. 4E

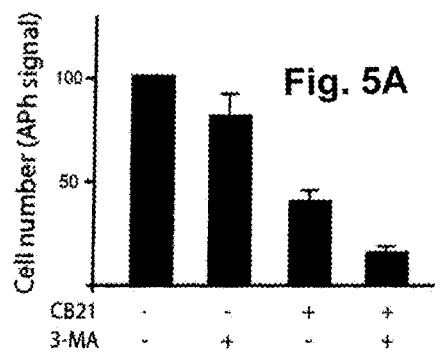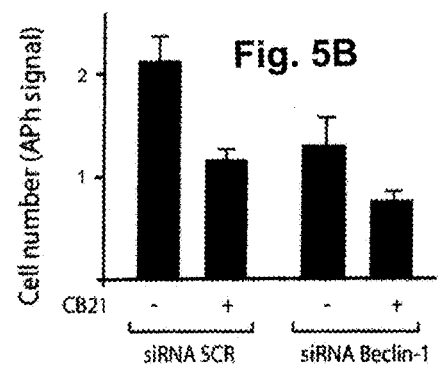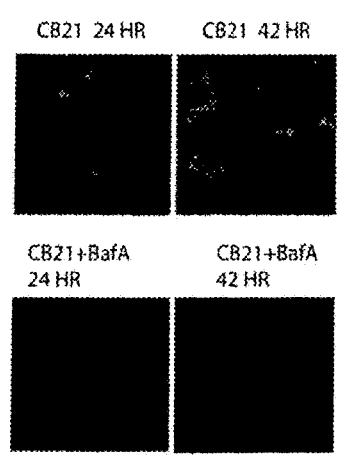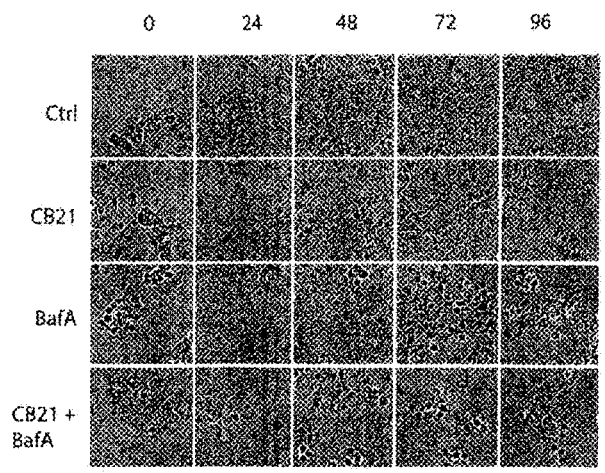
Fig. 5C
Fig. 5D
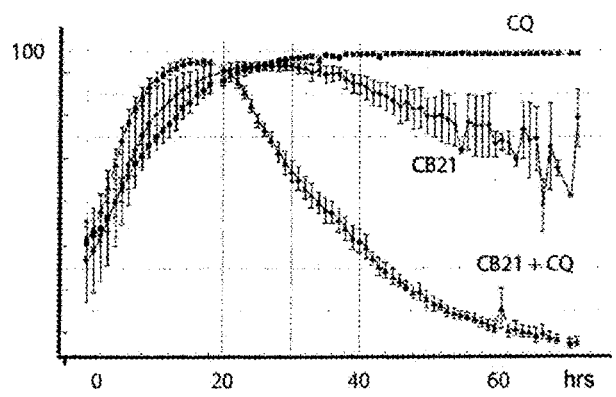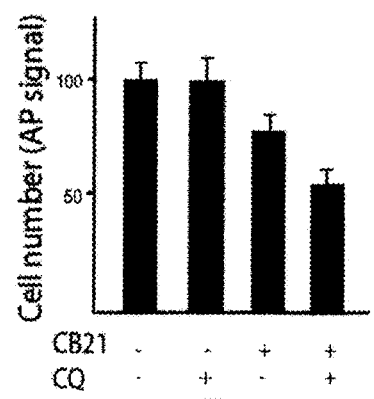
Fig. 5E
Fig. 5F

TREATMENT OF SOLID TUMOURS

FIELD OF THE INVENTION

The present invention relates to a treatment of a solid tumour, in particular a disseminated solid tumour, in a person affected by cancer and to a means for such treatment.

BACKGROUND OF THE INVENTION

New and effective anticancer drugs need to be developed for patients that suffer from disseminated cancer. Developing drugs for solid tumours is associated with specific problems due to complex biophysical and metabolic conditions in 3-D tumour tissue which may be difficult to mimic in experimental in vitro systems. Hypoxia and limited diffusion of nutrients is known to lead to quiescence and resistance to conventional anticancer agents and radiation therapy. Furthermore, anticancer drugs must be able to penetrate into tumour parenchyme to reach cancer cells at toxic concentrations. Some drugs that are in clinical use for the treatment of solid tumours show poor penetration into 3-D tumour masses, which may be one of the reasons for their limited efficacy (1). Multicellular spheroids (MCS) mimic human solid tumours better than 2-D monolayer cultures (2-4), and many clinically used drugs show limited potency on cancer cells grown as MCS (5, 6). Therefore, MCS are better suited than monolayer cultures for screening drugs active on solid tumours.

Cell death is often subdivided into three types of cell death: apoptosis (type I), autophagic cell death (type II) and necrosis (type III). Apoptosis is mediated by the activation of caspases. Autophagy is an evolutionarily conserved mechanism for degradation of long-lived cellular proteins and damaged cell organelles. The formation of autophagosomes is a main characteristic of autophagy. Autophagosome formation requires activation of class III phosphatidylinositol-3-kinase and is also dependent of two ubiquitin-like conjugation systems (Atg-Atg12 and Atg8) (7). Autophagy protects cells during conditions of nutrient deprivation, and cells undergo apoptosis when autophagy is inhibited (8-10). Morphological features of autophagy have also been observed during cell death under conditions of caspase inhibition (11).

SUMMARY OF THE INVENTION

According to the invention is disclosed the use of a cell permeable iron chelator, optionally in combination with an autophagy inhibiting agent, for treating a solid cancer tumour in a person.

According to the present invention is disclosed the use of a N-(1-pyridine-2-yl-methylidene)-N-(9H-1,3,4,9-tetraaza-fluoren-2-yl)-hydrazine or a pharmaceutically acceptable salt thereof of the general formula I, wherein R is H or methyl, $R^1$ is H or $C_1$-$C_4$ alkyl, $R^2$ is H or $C_1$-$C_4$ alkyl for treating a solid tumour in a person affected by cancer.

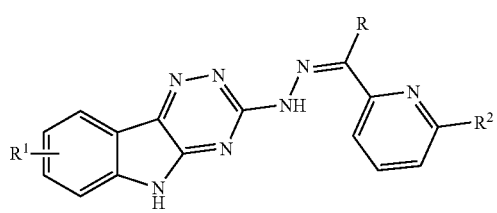

I

In this application, the compound of general formula I is intended to include any pharmaceutically suitable salt or complex or prodrug thereof.

It is particularly preferred for R to be methyl. It is preferred for both of R, $R^1$ to be methyl.

It is preferred for $R^1$ to be methyl, in particular 6-methyl or 8-methyl.

In preferred compounds of the invention N-(1-pyridine-2-yl-methylidene)-N-(9H-1,3,4,9-tetraaza-fluoren-2-yl)-hydrazine is substituted as follows:

| R | $R^1$ | $R^2$ |
|---|---|---|
| methyl | 8-methyl | H |
| methyl | H | H |
| methyl | 6-methyl | H |
| H | 6-methyl | H |
| H | 8-methyl | $CH_3$ |

According to a preferred aspect of the invention the compound of the general formula I in which $R^1$ is $C_1$-$C_4$ alkyl may be additionally substituted by $C_1$-$C_4$ alkyl at one of positions 6, 7 or 8 of the tetraazaflourenyl moiety not substituted by $R^1$.

According to a preferred aspect of the invention is disclosed a pharmaceutical composition comprising a compound of the invention and a pharmaceutical carrier. The pharmaceutical composition of the invention can be administered by any suitable route, such perorally or parenterally. Suitable carriers comprise dimethyl sulfoxide and aqueous media, such as mixtures comprising dimethyl sulfoxide and water. Preferred fluid carriers are those capable of dissolving the compound of the invention. Other preferred fluid carriers, in particular aqueous carriers, are those comprising the compound of the invention in finely dispersed form, such as in form of microparticles of a size of 10 μm or smaller.

According to another preferred aspect of the invention is disclosed a method of treating a solid cancer in a person, comprising administering to the person a pharmacologically effective dose of a compound of the invention or a pharmaceutically acceptable salt thereof. The pharmacologically effective dose is preferably administered comprised by the pharmaceutical composition of the invention.

The compound of the invention is a cell permeable iron chelator. While not wishing to bound by theory, the inventors believe the anti-cancer effect of the compound of the invention to be based on its iron-chelating properties.

According to a particularly preferred aspect of the invention the anti-tumour efficacy of an iron chelator, such the compound of the invention, is enhanced by an autophagy inhibiting agent. A preferred autophagy inhibiting agent is chloroquine. In view of this aspect is disclosed the use an autophagy inhibiting agent and a cell permeable iron chelator in combination in the treatment of a solid tumour. With "in combination" is understood the administration of the autophagy inhibiting agent and the cell permeable iron chelator in a close temporal relationship, such as at the same time or within a period of up to one day and even one week. The autophagy inhibiting agent and the cell permeable iron chelator can be administered in form of a pharmaceutical composition comprising them or in form of separate pharmaceutical compositions. If administered in form of a pharmaceutical composition, the combination comprises a pharmaceutically acceptable carrier.

In the combination of the autophagy inhibiting agent and the cell permeable iron chelator, the cell permeable iron chelator is preferably selected from N-(1-pyridine-2-yl-methylidene)-N-(9H-1,3,4,9-tetraaza-fluoren-2-yl)-hydrazine or a pharmaceutically acceptable salt thereof of the general formula I, wherein R is H or methyl and $R^1$ is H or $C_1$-$C_4$ alkyl, for treating a solid tumour in a person affected by cancer. It is particularly preferred for R to be methyl. It is preferred for both of R, $R^1$ to be methyl. It is preferred for $R^1$ to be in particular 6-methyl or 8-methyl.

Preferred iron chelating compounds of the invention for use in the combination comprise N-(1-pyridine-2-yl-methylidene)-N-(9H-1,3,4,9-tetraaza-fluoren-2-yl)-hydrazine of the general formula I, wherein is

| R | $R^1$ | $R^2$ | | Identified also by |
|---|---|---|---|---|
| methyl | 8-methyl | H | particularly preferred | CB21 |
| methyl | H | H | preferred | |
| methyl | 6-methyl | H | preferred | |
| H | 6-methyl | H | preferred | |
| H | 8-methyl | methyl | preferred | |

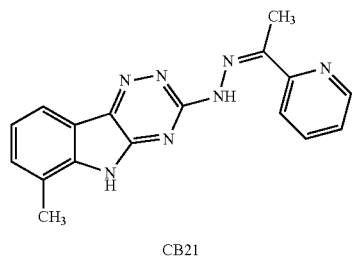

CB21

Further iron chelating compounds for use in combination with the autophagy inhibiting agent of the invention include deferoxamine, deferiprone, and deferasirox.

In the combination of the autophagy inhibiting agent and the cell permeable iron chelator, the autophagy inhibiting agent is preferably selected from chloroquine. Other preferred autophagy inhibiting agents comprise hydroxychloroquine, 3-methyladenine, adenosine, bafilomycin A1, 5-amino-4-imidazole carboxamide riboside, wortmannin, and viniblastine.

Further autophagy inhibitors for use in the invention are those of the general formula II

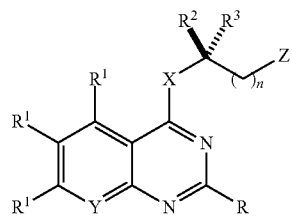

II disclosed in WO 2011/011522 A2, which is incorporated herein by reference.

According to the present invention is also disclosed a method of treating a solid tumour in a person affected by cancer, the method comprising administering to said person a pharmacologically effective dose of the combination of autophagy inhibiting agent and cell permeable iron chelator of the invention in a close temporal relationship, such as at the same time or within one day or one week. Administration may be by any suitable route, such as parenteral or per-oral in form of separate pharmaceutical combinations, one comprising the autophagy inhibitor and a pharmaceutically acceptable carrier, for instance dimethyl sulfoxide, or in a single pharmaceutical combination when administered at the same time, comprising a pharmaceutically acceptable carrier such as dimethyl sulfoxide.

According to a still further preferred aspect of the invention is disclosed a method of treating a solid cancer in a person, comprising administering to the person the combination of autophagy inhibiting agent and cell permeable iron chelator in pharmacologically effective dose, either simultaneously or in a close timely relationship, such as within an hour or a day or a week. Administration is preferably in form of the pharmaceutical composition(s) disclosed above, and by the parenteral or peroral or other suitable route.

The invention will now be described in more detail by reference to a number of preferred embodiments illustrated in a drawing comprising a number of figures.

SHORT DESCRIPTION OF THE FIGURES

FIG. 1 illustrates the in-vivo activity of CB21 on FaDu head-neck carcinoma xenografts. SCID mice carrying FaDu tumours were treated with mg/kg of CB21 and tumour volume was calculated.

Figure 2A:
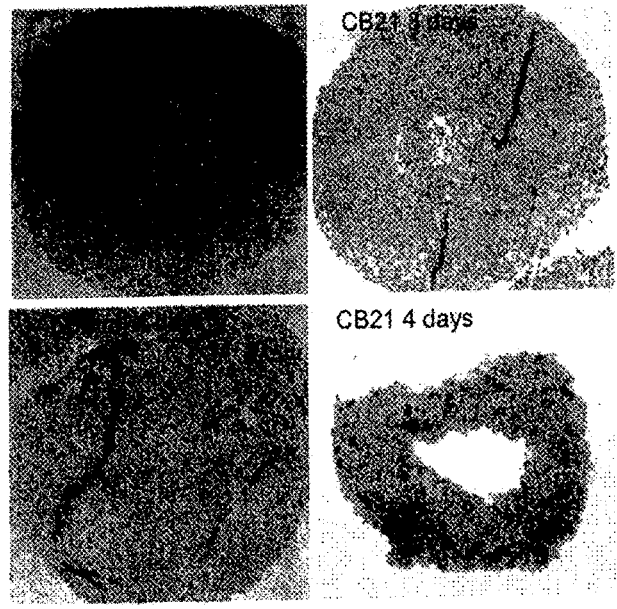
Figure 2D:
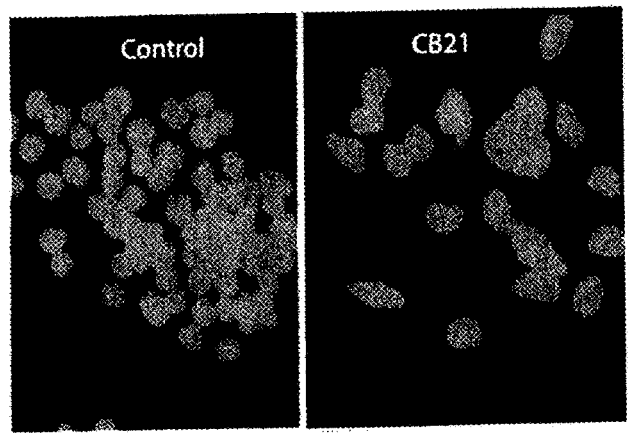
Figure 2H:
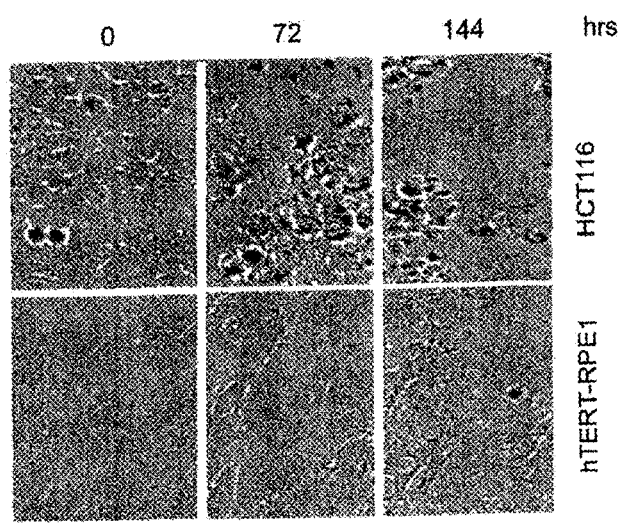
Figure 2B:
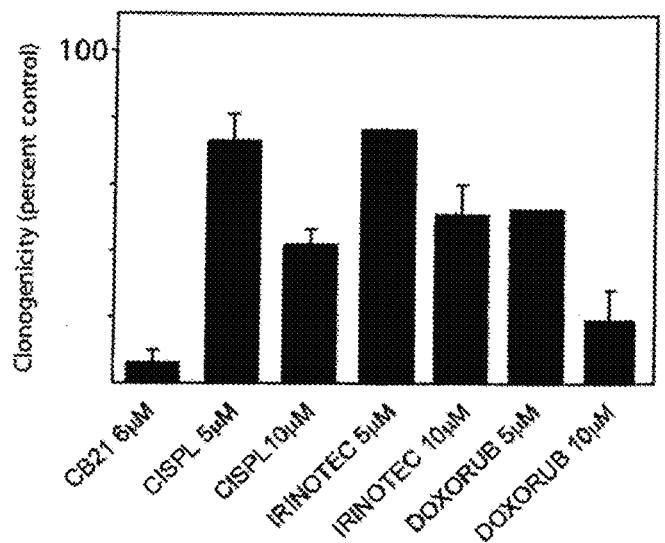
Figure 2C:
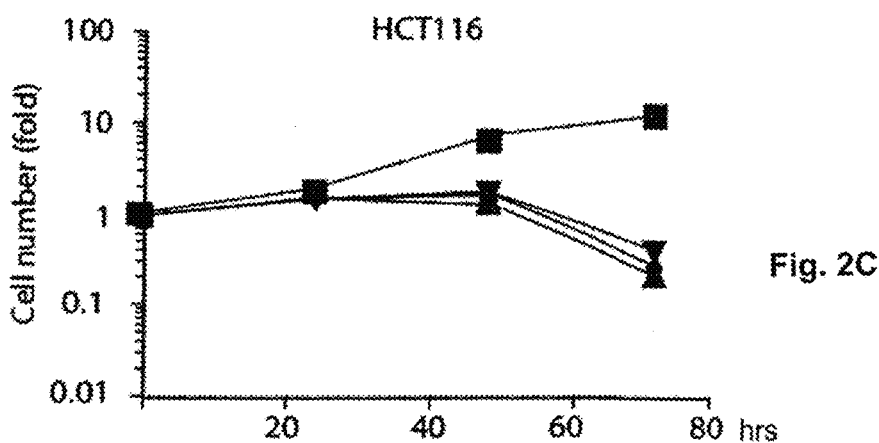
Figure 2E:
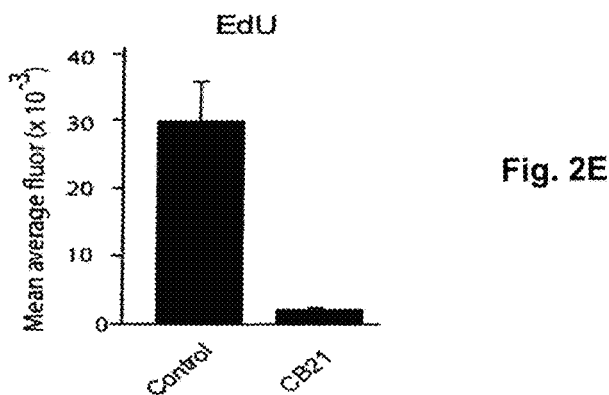
Figure 2F:
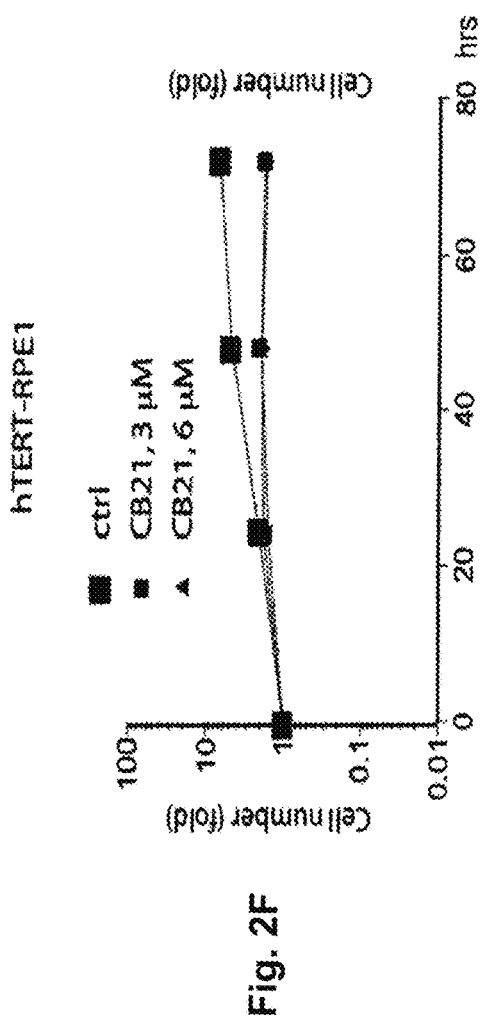
Figure 2G:
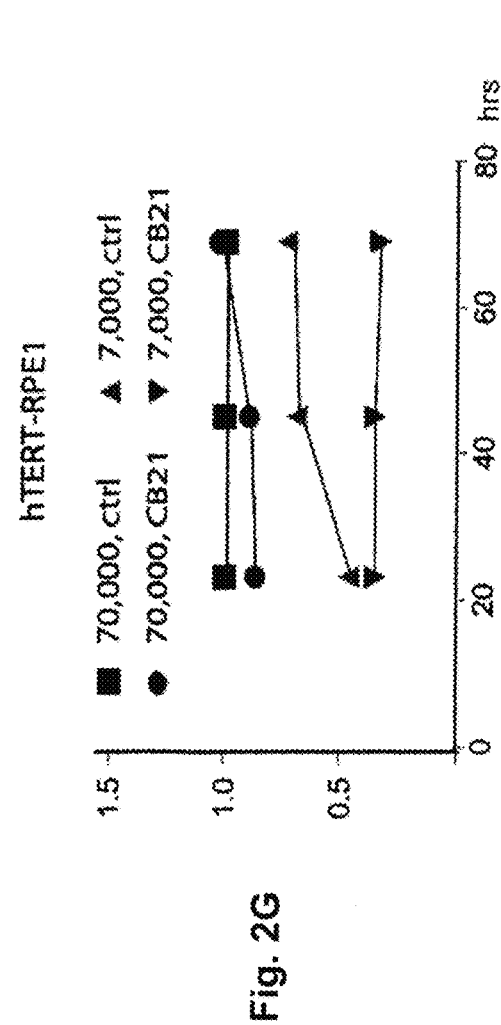

FIGS. 2A-2H illustrate the cytotoxicity of N-(1-pyridine-2-yl-ethylidene)-N-(9H-1,3,4,9-tetraaza-8-methyl-fluoren-2-yl)-hydrazine (in the following identified as "CB21") to HCT116 MCS and the therapeutic window of the cytotoxic effect. FIG. 2A: Morphology and caspase-3 induction in MCS treated with CB21. HCT116 MCS were treated for 6 hours with 6 µM CB21, followed by changing to drug-free medium and further incubation. MCS were sectioned and stained for active caspase-3. FIG. 2B: Clonogenic outgrowth of cells treated with the indicated compounds. FIG. 2C: Proliferation of monolayer HCT116 cells in the presence or absence of CB21. Cells were seeded at 7,000 cells/well in 96 well plates and treated with 3, 6 and 12.5 µM CB21. FIG. 2D: EdU (5-ethynyl-2'-deoxyuridine) incorporation into monolayer HCT116 cells 24 hours after addition of 6 µM CB21. Cells were incubated for 30 minutes with EdU, fixed and analyzed by ArrayScan. FIG. 2E: Quantification of EdU signal in the experiment shown in FIG. 2D. FIG. 2F: Proliferation of monolayer hTERTRPE1 cells in the presence or absence of CB21. Cells were seeded at 7,000 cells/well in 96 well plates and treated with 3, 6 and 12.5 µM CB21. FIG. 2G: CB21 does not affect the viability of confluent hTERTRPE1 cells. Cells were seeded at 7,000 or 70,000 per well in 96 well plates in the presence or absence of CB21. FIG. 2H: Morphology of HCT116 and hTER-TRPE1 cells after exposure to 6 µM CB21.

Figure 3A:
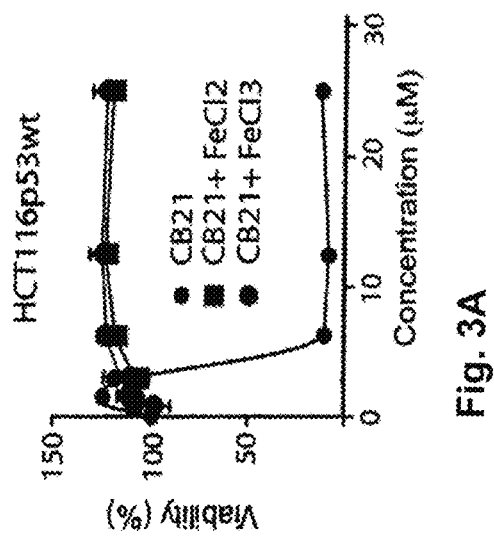
Figure 3B:
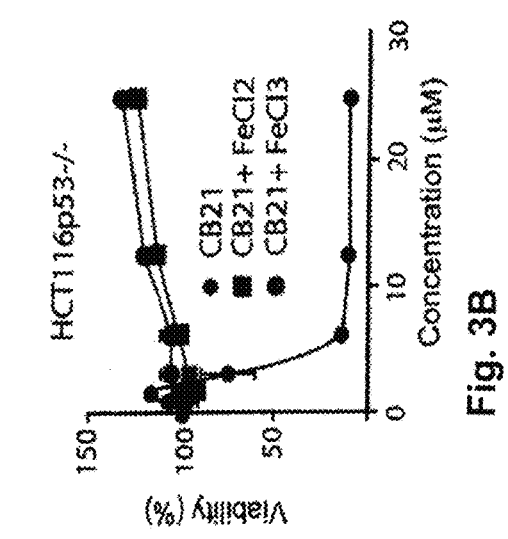

FIGS. 3 and 3A-3E illustrate that CB21 is a potent iron chelator. FIG. 3: Scores according to the Connectivity Map (Cmap) database. FIGS. 3A and 3B: Viability of cells treated with 6 µM CB21 in the presence or absence of iron chloride. FIG. 3A: HCT116 cells; FIG. 3B HCT116 p53−/− cells. FIG. 3C: Viability of HCT116 cells treated with different iron chelators.

FIG. 3D: Viability of HCT116 cells treated with 7 compounds with structures related to CB21. FIG. 3E: CB21 is the most effective of a series of related compounds in reducing MCS viability.

Figure 4F:
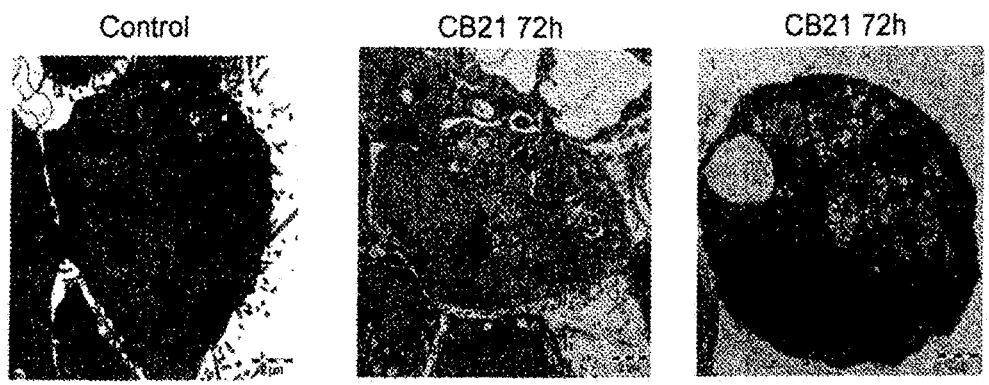
Figure 4G:
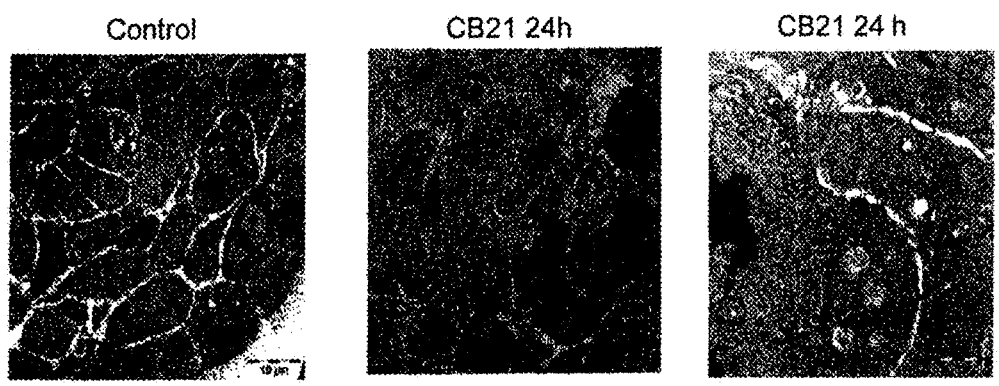
Figure 4H:
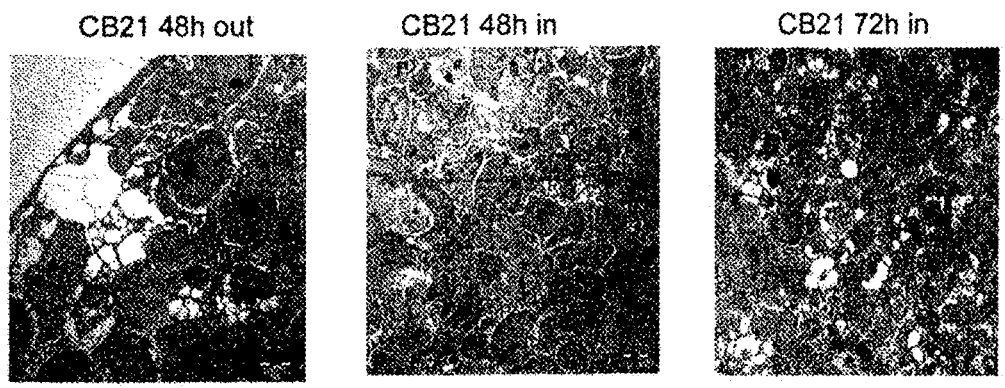

FIGS. 4A-4H illustrate the induction of autophagy by CB21 and other iron chelators. FIG. 4A: Morphology of monolayer HCT116 cells exposed to 6 µM CB21 for 6 hours and an additional 42 hours or 90 hours in drug-free medium. FIG. 4B: Staining of CB21-treated cells with an antibody to LC3. FIG. 4C: Induction of LC3-I and LC3-II protein by CB21 in monolayer and MCS HCT116. Cells were treated for 6 hours (6 µM), and then incubated further. Protein were extracted and subjected to western blot analysis. FIG. 4D: Induction of LC3-I and LC3-II protein by CB21 in monolayer and MCS hTERTRPE1 cells. FIG. 4E: Induction of LC3-I and LC3-II by different iron chelators. Cells were treated with VLX50 (50 μM); Deferasirox (60 μM), deferoxamine (200 μM), ciclopiroxolamine (15 μM), CB21 (5 μM), rapamycin (0.1 μM), NVP-BEZ235 (0.2 μM). FIGS. 4F-4H: Morphology of peripheral and core cells visualized by electron microscopy. MCS were treated for 6 hours with 6 μM C21 and incubated further in drug-free medium for the times indicated and sectioned. Note the appearance of swollen mitochondria at 24 hours of CB21 treatment.

FIGS. 5A-5F Illustrate that inhibition of CB21-induced autophagy increases CB21-cytotoxicity. FIG. 5A: HCT116 monolayer cells were treated with 6 μM CB21 and/or 10 μM 3-MA and cell viability was determined after 48 hours. FIG. 5B: HCT116 monolayer cells were transfected with siRNA to Beclin/Atg6 or control siRNA. After 24 hours cells were treated with 6 μM CB21 as indicated. FIG. 5C: Bafilomycin A (10 μM) inhibits formation of LC3 positive vesicles in CB21-treated cells. Cells were fixed and stained for LC3 after drug treatment at the times indicated. FIG. 5D: Bafilomycin A increases the cytotoxicity of CB21. Cells were treated with 6 μM CB21 and/or 10 μM bafilomycin A and cells were photographed at the times Indicated. FIG. 5E: Chloroquine increases the cytotoxicity of CB21 in monolayer culture. HCT116 cells were treated with 6 μM CB21 and/or 10 μM chloroquine. Cell proliferation was monitored by calculation of culture confluency.

FIG. 5F: Chloroquine increases the cytotoxicity of CB21 in MCS culture. Cell viability was determined using the acid phosphatase test. Note that background levels of acid phosphatase activity was observed in HCT116 MCS cultures containing no viable cells (generally ~30%), probably due to enzyme trapping.

Figure 6A:
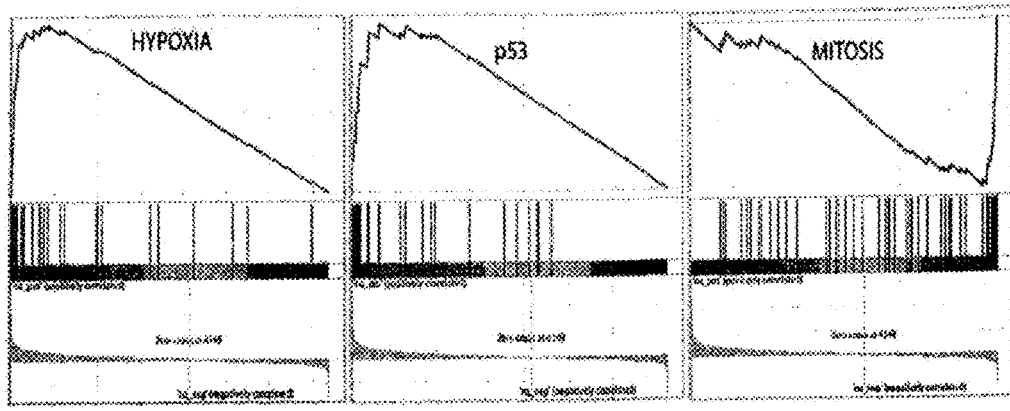

FIGS. 6A-6E Illustrate that CB21 induces a p53 and hypoxia response. FIG. 6A: Gene expression profile induced by CB21 were analyzed by Affymetrix microarrays and the representation of genes associated with hypoxia, p53 networks and mitosis is shown.

Figure 6B:
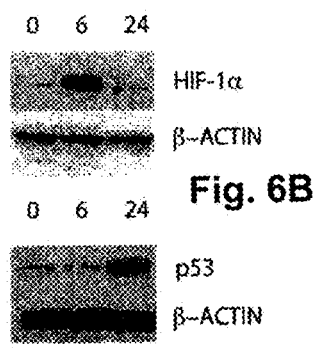
Figure 6D:
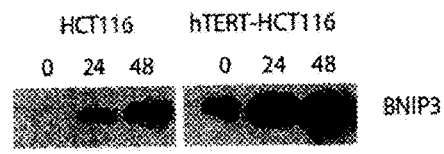
Figure 6C:
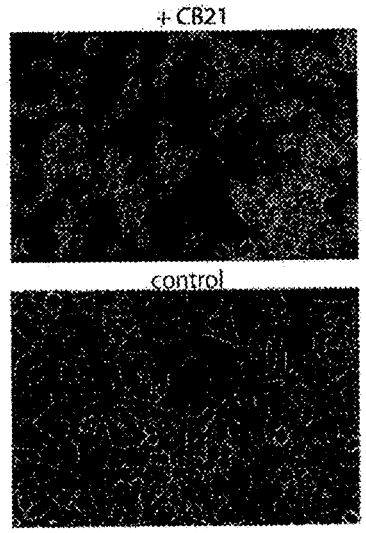
Figure 6E:
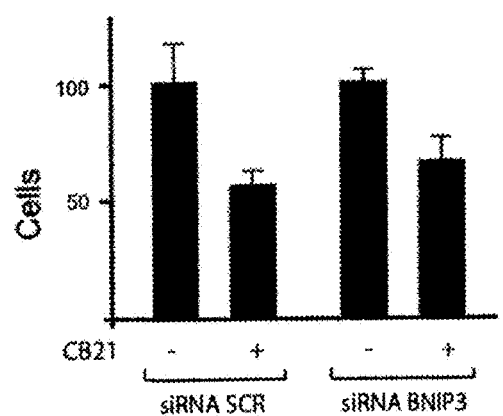

FIG. 6B: Analysis of p53 and HIF-1a by western blotting. HCT116 cells were treated with 6 μM CB21 for the times indicated. FIG. 6C: Induction of a HIF-1a-promoter driver GFP reporter by CB21. FIG. 6D: Induction of BNIP3 by CB21 in HCT116 and hTERT-RPE1 cells. FIG. 6E: Knockdown of BNIP3 does not affect CB21-induced cell death. HCT116 cells were transfected with siRNA to BNIP3 or control siRNA and treated with 6.25 μM CB21 after 24 hours. Viability was determined after 48 hours using the acid phosphatase assay.

Figure 7C:
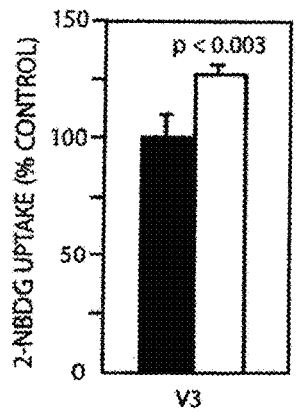
Figure 7C:
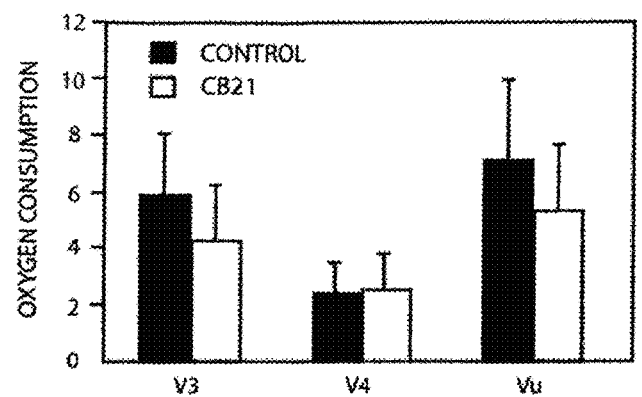
Figure 7C:
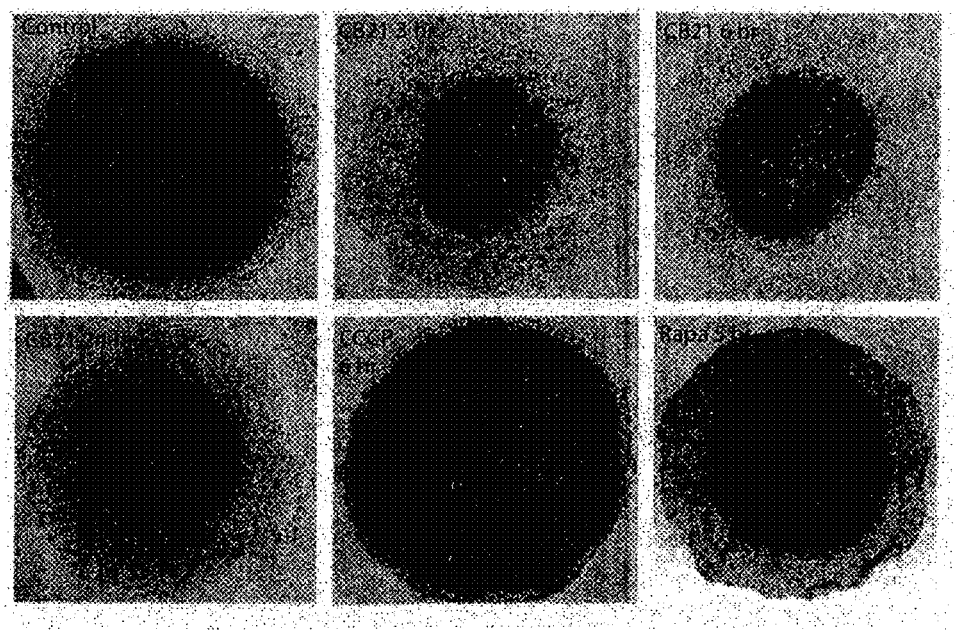
Figure 7D:
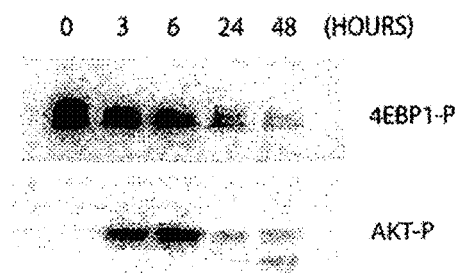

FIGS. 7A-7D illustrate that CB21 reduces respiration and inhibits mTOR. FIG. 7A: Effect on glucose transport. FIG. 7B: CB21 reduces oxygen consumption. FIG. 7C: CB21 reduces hypoxia in HCT116 MCS. HCT116 MCS were treated as indicated and processed for pimonidazole immunohistochemistry. Note that CB21 reduces the area staining positive for pimonidazole adducts (<10 mm Hg O2). FIG. 7D: CB21 inhibits phosphorylation of 4EBP1. HCT116 cells were treated with CB21 for the times indicated and protein extracts were processed for western blotting. Reduction in 4EBP1 phosphorylation and induction of AKT phosphorylation should be noted.

Figure 8A:
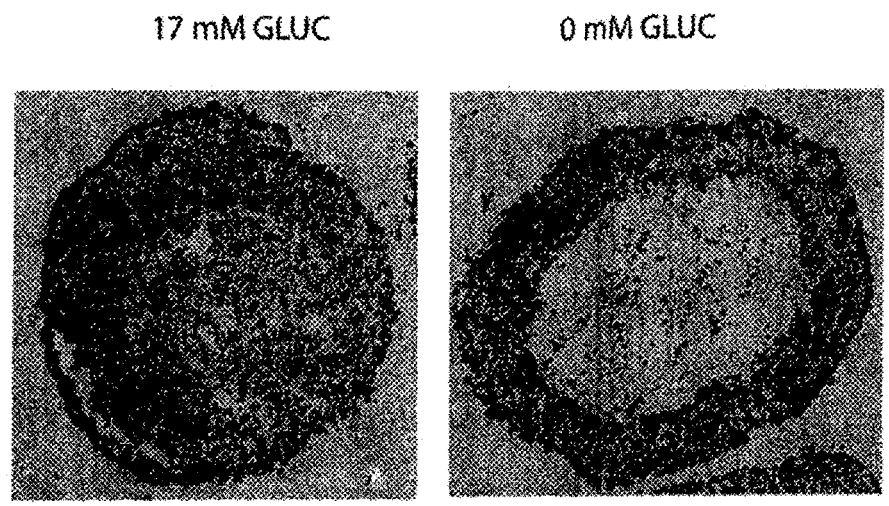
Figure 8B:
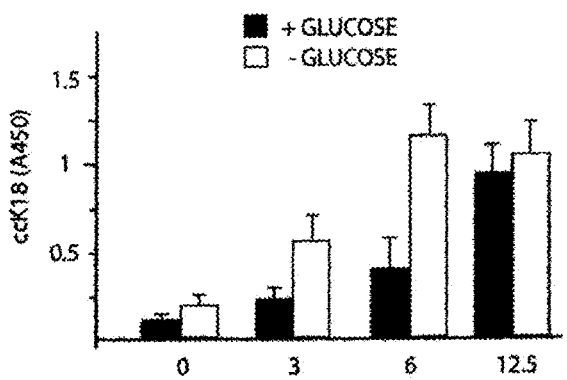
Figure 8C:
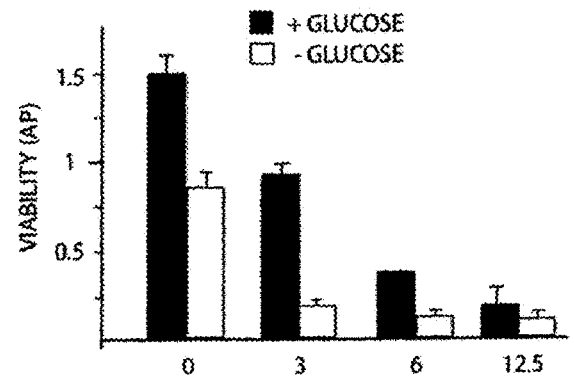

FIGS. 8A-8C illustrate that CB21 cytotoxicity is enhanced by glucose starvation. FIG. 8A: Morphology of HCT116 MCS after incubation in the presence or absence of glucose for 24 hours. FIG. 8B: HCT116 monolayer cells were treated with different concentrations of CB21 in glucose-containing or glucose-free medium. The levels of caspase-cleaved K18 was determined using M30 CytoDeath ELISA. FIG. 8C: HCT116 monolayer cells were treated as in FIG. 8B. Viability was determined using the acid phosphatase assay.

DESCRIPTION OF PREFERRED EMBODIMENTS

Materials and Methods

Compounds of the invention were obtained from compound libraries. They can be prepared according to methods described in the literature, such as in WO 02/089809, or by their non-inventive modifications. The compounds were dissolved in DMSO. A final concentration of 0.5% DMSO was reached in cell cultures.

Cell Culture, Generation of MCS and Screening.

HCT116 colon carcinoma cells were maintained in McCoy's 5A modified medium/10% fetal calf serum at 37° C. in 5% $CO_2$. MCS were prepared using a modification of our previously described method (12). A cell suspension containing 10,000 cells (200 μl) was added to each well of poly-HEMA coated 96 well plates. The wells were then overfilled by adding an additional 170 μl media to acquire a convex surface curvature. Plasticine spacers (3 mm) were placed in the corners of each plate to prevent the lids from touching the media. The plates were then inverted in order to allow the cells to sediment to the liquid/air interface and incubated in gentle shaking. After 24 hrs incubation the plates were returned to normal. First excess media was removed by aspiration and then plasticine spacers. The plates were incubated for 4 days prior to drug treatment. After 24 hours of drug treatment, NP40 was added to the culture medium to a concentration of 0.1% to extract caspase-cleaved K18 from MCS and to include material released to the medium from dead cells. Caspase cleaved keratin-18 (K18-Asp396) was determined using 25 mL medium/extract using the M30 CytoDeath ELISA assay (a variant of the M30-Apoptosense® ELISA (13) developed for in-vitro use (Peviva AB, Bromma, Sweden)).

Viability measurements were performed by the acid phosphatase (APH) method described by Friedrich et al. (14). Background activity was subtracted.

hTERT-RPE1 cells were obtained from Clontech Laboratories, Mountain View, Calif. hTERT-RPE1 is an immortalized human retinal epithelial cell line that stably expressed human telomerase reverse transcriptase (hTERT).

Evaluation of DNA Synthesis.

The fluorescence microscope ArrayScan V HCS system (Cellomics Inc., Pittsburgh, Pa., USA) was used to determine EdU incorporation. Before addition of test compounds HCT116 cells were seeded into 96-well plates (PerkinElmer Inc., Wellesley, Mass., USA) and left to attach over night. Cells were treated with CB21 for 24 h or with vehicle control. Cells were stained using Click-iT EdU HCS assay (C10354, Invitrogen, Molecular Probes Inc, OR, USA) according to the manufacturer's instructions. Processed plates were loaded in the ArrayScan and analyzed. Images were acquired for each fluorescence channel, using suitable filters with 10× objective and in each well at least 1000 cells were analyzed. Average total intensity in the BdU channel was measured. Results are shown as average of two independent experiments, each performed in duplicate wells and shown as mean±SD.

Immunological Assays.

MCS produced by the hanging drop method in 96 well plates were fixed in paraformaldehyde, dehydrated, embedded in paraffin and sectioned. Each sample contained 32 MCS (MCS from each 96 well plate were pooled into 3 groups). The sections were deparaffinized with xylene, rehydrated and microwaved, and then incubated overnight with the monoclonal primary antibodies diluted in 1% (weight/volume) bovine serum albumin and visualized by standard avidin-biotin-peroxidase complex technique (Vector Laboratories, Burlingame, Calif., USA). Counterstaining was performed with Mayer's haematoxylin. Antibody MIB-1 (against the nuclear proliferation-associated antigen Ki67) was obtained from Immunotech SA, Marseille, France and used at a dilution of 1:150; antibody against active caspase-3 was obtained from Pharmingen and used at a dilution of 1:50.

Western Blotting.

Cell extract proteins were resolved by Tris-Acetate PAGE gels (Invitrogen, Carlsbad, Calif.) and transferred onto a polyvinylidene difluoride (PVDF) membrane. The membranes were incubated overnight with antibodies, washed and incubated with HRP-conjugated anti-rabbit Ig (Amersham Biosciences, Little Chalfont, UK) for 1 h. Peroxidase activity was developed by SuperSignal West Pico (Pierce Biotechnology, Rockford, Ill.) according to manufacturer's instructions.

Connectivity Map.

The Connectivity Map (CMAP) (www.broad.mit.edu/cmap) build 02 contains genome-wide expression data for 1300 compounds (6100 instances, including replicates, different doses and cell lines). The original protocol using MCF-7 breast cancer cells as described by Lamb et al (15) was followed. Cells were plated in 6-well plates at a density of 0.4×106 cells per well and left to attach for 24 h, followed by exposure to NSC76022, NSC620358 or NSC647889 at a final concentration of 10 µM, or to vehicle control (DMSO). After 6 h treatment, the cells were washed with PBS. Total RNA was prepared using RNeasy miniprep kit (Qiagen, Chatsworth, Calif.,). Starting from two micrograms of total RNA, gene expression analysis was performed using Genome U133 Plus 2.0 Arrays according to the GeneChip Expression Analysis Technical Manual (Rev. 5, Affymetrix Inc., Santa Clara, Calif.). Raw data was normalized with MAS5 (Affymetrix) and gene expression ratios for drug treated vs. vehicle control cells were calculated to generate lists of regulated genes. Filter criteria were present call for all genes in the treated cell line and an expression cut-off of at least 100 arbitrary expression units. For CMAP compatibility reasons only probes present on HG U133A were used. To retrieve a ranked compound list the 40 most up and down regulated genes (i.e. probes) for each compound were uploaded into the CMAP and compared with the 6100 instances in the CMAP database.

Oxygen Consumption.

Measurement of respiration was performed as described (16). Succinate (5 mM) in the presence of rotenone (2 mM), malate+pyruvate (5 mM each) and TMPD (0.5 mM)+ascorbate (1 mM) were used as mitochondrial substrates. Changes in the oxygen concentration were monitored with an oxygen electrode (Hansatech Instruments, Norfolk, UK) and analyzed with the OxygraphPlus software (Hansatech Instruments, Norfolk, UK). Basal V4 respiration in cells was estimated in the presence of 1 M atractyloside, which blocks ADP entry into mitochondria.

Treatment of Mouse Xenografts.

When HCT116 tumours in SCID mice had grown to a size of 200 mm$^3$ the mice were injected with drugs i.p., and tumour size measured daily.

Example 1. The Compound of the Invention Induces Apoptosis and Reduces Viability of MCS Treatment of MCS with CB21 for 6 h followed by incubation for 96 h in drug-free medium resulted in MCS of smaller size with central areas of necrosis (FIG. 2a). Caspase-3 induction was modest compared to NSC647889. Importantly, treatment of MCS for 6 hours with CB21 reduced the clonogenicity to <5% (FIG. 2b). The decrease in clonogenicity was stronger than that observed for cisplatin, irinotecan and doxorubicin (despite the use of concentrations of 5-10 µM; >10-fold the IC50 of these compounds in monolayer cultures). Treatment of monolayer HCT116 cells with CB21 resulted in a slight increase in cell numbers between 0 to 24 h, followed by loss of cells (FIG. 2c). Examination of 5-ethynyl-2'-deoxyuridine incorporation (EdU) in CB21-treated cells showed that DNA synthesis was almost completely abrogated at 24 hours (FIG. 2d, 2e). CB21 was equally effective on cells where the p53 tumour suppressor gene had been disrupted as on cells expressing wt p53 (FIG. 2b). The response of immortalized human epithelial cells (hTERT-RPE1 cells) differed from that of HCT116 cells. The growth of these cells was arrested, but cell numbers were not reduced (FIG. 2f). When hTERT-RPE1 cells were plated at high density (70,000 cells/well), essentially no cell loss was observed after treatment with CB21 (FIG. 2g). This difference in response to CB21 between HCT116 and hTERT-RPE1 cells is shown in FIG. 2h.

Example 2. The Compound of the Invention is a Cell Permeable Iron Chelator

To generate hypotheses regarding the mechanism of action of CB21, the Connectivity Map (CMap) (15), a compendium of gene expression signatures from drug-treated cell lines, was used. The changes in gene expression elicited by CB21 were most similar to those of ciclopiroxolamine (CPX), an antimycotic agent with iron chelating capacity (17) (FIG. 3a). To test whether the cytotoxic activity of CB21 was dependent on iron depletion, iron chloride was added to HCT116 cells prior to the addition of CB21. Iron chloride was found to totally abrogate the effect of CB21 (FIG. 3b), both on HCT116 cells expressing wtp53 as on HCT116 cells where the p53 gene has been disrupted.

The anti-proliferative activity of CB21 was compared with that of other known iron chelators. CB21 was found to be more potent than VLX50, deferasirox, ciclopiroxolamine, deferoxamine (FIG. 3c). Structure-activity relationships were examined by use of a number of structurally related compounds (FIGS. 3d, 3e). These studies showed that CB21 was the most effective compound in both monolayer and MCS cultures.

Example 3. The Compound of the Invention Induces a Widespread Autophagic Response The anti-tumourigenic activity of iron chelators is generally attributed to inhibition of ribonucleotide reductase, leading to inhibition of cell proliferation (18). MCSs contain mostly non-proliferating cells. The finding of induction of cytotoxic effects on MCSs by the iron chelator CB21 thus was unexpected. The mechanism(s) of action was studied in more detail. Visual inspection of CB21-treated cells revealed that cells contained multiple large cytoplasmic vesicles (FIG. 4a). These vesicles stained positively with an antibody to microtubule associated protein 1 light chain 3 (LC3), suggesting that they were associated with autophagy. LC3 staining was observed at 24 h and was stronger at 42 h (FIG. 4b). Western blot analysis showed that treatment of HCT116 monolayer cells with CB21 induced a strong increase in the levels of both LC3-I and LC3-II (FIG. 4c).

LC3-II (the PE-conjugated form of LC3) is a protein marker regarded to be most reliably associated with autophagosomes (19). LC3-II levels were strongly induced by CB21 also in HCT116 MCS (FIG. 4c). CB21 also induced LC3-II in hTERT-RPE1 cells, but the level of induction was much weaker compared to HCT116 cells (FIG. 4d). This result shows that the extent of CB21-induced autophagy correlates to the cytotoxic effect of the compound in these two cell types.

HCT116 cells were treated with cytotoxic concentrations of different iron chelators for 24 h. Induction of LC3-I and LC3-II was observed in all instances, showing that LC3 induction was a general effect of iron chelators (FIG. 4e). Induction of LC3-I and -II by iron chelators was much stronger compared to that observed after treatment with rapamycin or NVP-BEZ235 (no induction observed at 24 h, weak induction at 6 h). For examination of whether CB21 is able to induce cellular changes in the inner core cells of the MCS, HCT116 MCS were treated with CB21 for 6 h, washed and incubated for different time periods, fixed, sectioned, and examined by electron microscopy. Large vesicles were observed in cells starting at 24 h after treatment (FIG. 4f). Notably, a common feature of CB21-treated MCS was the early appearance of enlarged and swollen mitochondria (FIG. 4f). Most importantly, massive vacuolization occurred in a time-dependent manner not only in cells in the MCS periphery but also in the center of the MCS (FIG. 4f). It was concluded that CB21 induces the formation of vesicles in the cells of the central cores of MCS, found to be resistant to apoptosis, and that this response was associated with loss of viability of these cells.

Example 4. Blocking Autophagy or Autophagosome-Lysosome Fusion Enhances Cell Death by the Compound of the Invention Autophagy is generally considered to be a survival response to stress conditions but may also be a mechanism of programmed cell death (20, 21). To examine the effects of different inhibitors of autophagy on CB21-induced cell death, the cytotoxic effect of CB21 was potentiated by 3-MA (FIG. 5a), a PI3K inhibitor commonly used as an inhibitor of autophagy. Next a knock-down of Beclin/Atg6 using siRNA was performed. This resulted in almost complete knock-down of the expression of this protein. Beclin/Atg6 knock-down reduced the viability of HCT116 cells by ~50%; viability was further reduced by CB21 toxicity (FIG. 5b). Examination of the effect of Bafilomycin A, an antibiotic that prevents fusions of autophagosomes and lysosomes, demonstrated that Bafilomycin A suppresses the appearance of large cytoplasmic LC3-II positive vesicles in HCT116 cells (FIG. 5c). Whereas bafilomycin A induced cytotoxicity at ~72 hours, the combination of bafilomycin A and CB21 cytotoxicity was observed earlier (~48 hours) (FIG. 5d). These findings show that inhibition of autophagy potentiates the cytotoxic effect of the compound of the invention, and that the large vesicles observed in CB21 treated cells are caused by the fusion of autophagosomes and lysosomes.

Chloroquine (CQ) is a lysosomotropic agent widely used to inhibit the maturation of autophagosomes into degradative autolysosomes (22). CQ has no effect on its own on the proliferation of HCT116 cells. The combination of CQ and CB21 resulted in a strong potentiation of cell death on monolayer HCT116 cells (FIG. 5e). Examination of cytotoxicity to MCS of the combination of CQ and CB21 revealed an effect potentiated in comparison with the effect of either CQ or CB21 on MCS (FIG. 5f).

Example 5. LC3 Induction is not Mediated by BNIP3

CB21 induced a number of hypoxia responsive genes and also a number of genes known to be regulated by p53 (FIG. 6a). Induction of HIF-1a and p53 protein levels by Western blotting (FIG. 6b) was confirmed. A large induction was also observed using a reporter cell line where GFP is regulated by the HIF-1a promoter (FIG. 6c).

Among different genes strongly induced by CB21 was noted the gene encoding the BH3-only protein BNIP3. BNIP3 is a known target of HIF-1 a (23). BNIP3 expression has been reported to induce extensive cytoplasmic vacuolization and autophagy (24). CB21 was found to induce the expression of BNIP3 protein in HCT116 cells (FIG. 6d). BNIP3 expression was, however, also strongly induced by CB21 in hTERT-RPE1 cells (FIG. 6d). This finding is not consistent with BNIP3 being a presumed mechanism of CB21-induced autophagy. Knock-down of BNIP3 using siRNA did not decrease induction of LC3-II and cell death by CB21 (FIG. 6e).

Example 6. The Compound of the Invention Inhibits Oxygen Consumption and Decreases mTOR Activity The results described above suggest that autophagy is induced as an attempt to rescue cells from toxic insults induced by CB21. Since a number of key proteins involved in cellular energy metabolism contain Fe—S complexes (25), the present inventors hypothesized that iron chelation by CB21 might lead to disturbances in cell metabolism that would trigger autophagy. To evaluate this hypothesis the effect of CB21 on intracellular levels of ATP was examined. However, no decrease of intercellular ATP levels at concentrations that induce autophagy could be observed nor could an induction of the phosphorylation of AMPK (AMP-activated protein kinase) be detected (not shown). Next, a possible affectation of glucose transport by CB21 was followed by flow cytometry using the fluorescent d-glucose analog 2-[N-(7-nitrobenz-2-oxa-1,3-diazol-4-yl)-amino]-2-deoxy-d-glucose (2-NBDG). As shown in FIG. 7a, a 25% increase in 2-NBDG uptake was observed in CB21-treated cells.

Examination of the effect of CB21 on cellular oxygen consumption revealed that in HCT116 monolayer cultures, V3 (state 3) and Vu (uncoupled) respiration did significantly decrease (p<0.05) after 6 hours of CB21 treatment (FIG. 7b). To examine whether respiration in tumour cells in the MCS is affected by CB21 an indirect approach was used. It is known that inhibition of mitochondrial respiration leads to increased tissue oxygen tension, which can be visualized as decreased pimonidazole staining (26). It was found indeed that the area of sectioned MCS staining positive with pimonidazole was ~50% of control in CB21-treated MCSs (FIG. 6C; Table). The effect was observed after 3 hours of drug exposure and persisted at 24 hours (FIG. 7c). As a control, HCT116 monolayer cultures were treated with the mitochondrial uncoupling agent carbonylcyanide-3-chlorophenylhydrazone, CCCP, known to increase oxygen consumption. As expected, MCS treated with CCCP displayed a larger of area of pimonidazole staining (FIG. 7c; Table).

TABLE

Quantification of pimonidazole staining of spheroids

| Sample | Conc. | Time/h | Pimonidazole positive area (%) | S.D. |
|---|---|---|---|---|
| Control | | | 63 | 13.0 |
| CB21 | 6.25 µM | 3 | 31.8 | 4.0 |
| Rapamycin | 10 nM | 5 | 42.2 | 5.2 |
| CCCP | 10 µM | 6 | 79.9 | 4.3 |

The mammalian target of rapamycin (mTOR) is a serine/threonine kinase regulating cell growth in response to nutrient status. It is well established that metabolic stress affects the activity of the mTOR pathway (27). The mTOR pathway regulates mitochondrial oxygen consumption and oxidative capacity (28, 29). In order to determine whether the decreased oxygen consumption observed after CB21 treatment was associated with mTOR inhibition, phosphorylation of the mTOR substrate 4EBP1 was examined. As shown in FIG. 7D, 4EBP1 phosphorylation is inhibited by CB21. The decrease in phosphorylation is associated with an increased AKT-phosphorylation. Inhibition of mTORC1 is known to release a negative feedback loop involving, resulting in strong Akt activation (30). To test whether mTOR inhibition would reduce oxygen consumption, HCT116 MCS was treated with rapamycin (a specific pharmacological inhibitor of mTOR-raptor complex formation) and stained sections with pimonidazole. A reduction of pimonidazole staining was observed, although not as strong as with CB21 (FIG. 7c; Table 1).

These findings prompted examination of whether direct inhibition of mTOR does lead to similar effects as by CB21. For these experiments was used the dual PI3K/mTOR inhibitor NVP-BEZ235, a compound in clinical trials. Importantly, NVP-BEZ235 was found to decrease 4EBP1 phosphorylation in HCT116 cells grown both under monolayer or MCS conditions (FIG. 7d). In contrast to CB21, NBPBEZ235 did not affect the viability of the cells in the core of the MCS.

Example 7. Cell Death Induced by the Compound of the Invention is Enhanced by Glucose Starvation Approximately 50% of cellular ATP production in tumour cells is by oxidative phosphorylation (31). Oxygen consumption has been reported to decrease in the interior regions of tumour MCS, possibly as a consequence of decreased proliferative activity (32, 33). Other investigators have found that oxygen consumption is rather uniform in viable regions of MCS (34); it has been reported that fibroblast clones at the same stage of transformation may have quite distinct metabolic activity in MCS culture (33). Even in the event of low cellular oxygen consumption in the cells of the central core, a further decrease induced by CB21 is expected to lead to an increased dependence of glucose. Whereas monolayer cells may compensate increased glucose dependence by increased uptake (as shown in FIG. 8a), glucose will be limiting in MCS. As shown in FIG. 8a, HCT116 MCS core cells are dependent on glucose for survival: glucose depletion leads necrosis of central areas, an effect is reminiscent of that of CB21 (FIG. 2). Based on these considerations it was tested whether glucose starvation increases the sensitivity of HCT116 monolayer cells to CB21. This was indeed the case: glucose starvation decreased cell viability and increased apoptosis by CB21. These findings are likely to at least partly explain the sensitivity of central core cells to CB21.

Example 8. Anti-Tumour Activity of the Compound of the Invention

The in-vivo anti-tumour activity by CB21 was examined in the HCT116 model. Tumours were allowed to grow to a size of 0.2 mL and then treated with CB21. A clear anti-tumour effect of the compound CB21 was observed (FIG. 1).

A number of iron chelators have been developed that exhibit anti-tumour activity, including Triapine (35), Tachpyr (36) and Trensox (37). Iron is important for many metabolic reactions, including the formation of deoxyribonucleotides from ribonucleotides by ribonucleotide reductase (38). In the absence of Fe, cells cannot progress from the G1 to the S phase of the cell cycle, explaining the anti-proliferative action of CB21 on both HCT116 and hTERT-RPE1 cells observed. Since iron chelators are principally regarded as specific to proliferating cells, the identification of an iron chelator in a screen for agents that show cytotoxicity on MCS was not anticipated. Further investigations revealed possible mechanisms for the effects of CB21 on non-proliferating cells in MCS cores. It was furthermore found that CB21 decreased oxygen consumption of HCT116 and hTERT-RPE1 cells, as observed both by direct measurement and by using pimonidazole staining of MCS. It is known that mitochondrial oxygen consumption and oxidative capacity is regulated by the mTOR pathway (28, 29). It has also been reported that the iron chelator deferasirox inhibits mTOR signaling (39). CB21 was indeed found to inhibit phosphorylation of 4EBP1 and to lead to a upregulated AKT phosphorylation. The inhibition of mTOR signaling by deferasirox has been ascribed to induction of REDD1 (also referred to RTP801), a gene induced by hypoxia, which in turn activates the TSC2 protein (40). It is conceivable that the effect of CB21 on oxygen consumption is at least partly mediated by this mechanism. Another possibility is that metabolic stress induced by iron depletion affects the activity of the mTOR pathway by some other mechanism.

Another effect of CB21, shared by other iron chelators (41), is the induction of LC3 positive cytoplasmic vesicles and LC3-II protein. LC3 induction was found to be much less pronounced in hTERT-RPE1 cells. The induction of LC3-II by iron chelators was significantly stronger than that observed with mTOR inhibitors, suggesting that LC3-II induction was not mediated exclusively by mTOR inhibition. It was found that the PI3K/mTOR inhibitor NVP-BEZ235 does not induce detectable cytotoxic effects on cells in HCT116 cores (Hernlund et at., unpublished), again suggesting mTOR inhibition not being the only factor responsible for autophagy induction and cell death by CB21. The decreased oxygen consumption observed after CB21 treatment should lead to increased dependence of glucose for ATP production, similarly to what has been reported for rapamycin (42). This proposition seems to be confirmed by the observation that the population of cells present in the MCS core showed signs of constitutive ER stress (Grp78 positive), a condition probably induced by hypoxia and limited glucose supply. Glucose starvation of MCS induced cell death of the core cells, consistent with the concept that survival of this cell population is dependent on glucose. The increased dependence of glucose observed after treatment with CB21 is very likely contributing to cell death of the population of core cells. Apoptosis did not appear to be the main mechanism of cell death by CB21, as evidenced by weak caspase-3 induction compared to the strong induction of caspase-3 in peripheral cells (not shown). Conditions of poor cellular energy status may lead to resistance to apoptosis (also explaining the resistance of core cells to NSC647889-induced apoptosis (not shown). It seems that CB21 induces increased glucose dependence of HCT116 cells, and that this leads to decreased viability of hypoxic cells in MCS cores.

Autophagy is a catabolic degradation response to metabolic stress, which strives to maintain homeostasis through degradation of proteins and organelles. PI3K-Akt-mTOR, LKB1-AMPK-mTOR and p53 are the main regulators of the autophagic pathway. Autophagy is believed to be involved in mediating resistance of cancer cells to anticancer therapy and to be an attractive therapeutic target in anticancer drug resistance (20, 43). CB21 induced a remarkable autophagic response, characterized be strong LC3-I and -II induction. The present invention reveals inhibition of autophagy to potentiate the cytotoxicity of CB21.

REFERENCES

1. Tannock I F et al. *Limited penetration of anticancer drugs through tumour tissue: a potential cause of resistance of solid tumours to chemotherapy*. Clin Cancer Res 2002; 8:878-84.
2. Sutherland R M and Durand R E. *Radiation response of multicell spheroids—an in vitro tumour model*. Curr Top Radiat Res Q 1976; 11:87-139.
3. Mueller-Klieser W. *Multicellular spheroids. A review on cellular aggregates in cancer research*. J Cancer Res Clin Oncol 1987; 113:101-22.
4. Zietarska M et al. *Molecular description of a 3D in vitro model for the study of epithelial ovarian cancer (EOC)*. Mol Carcinog 2007; 46:872-85.
5. Smalley K S et al. *Life isn't flat: taking cancer biology to the next dimension*. In Vitro Cell Dev Biol Anim 2006; 42:242-7.
6. Frankel A. et al. *Abrogation of taxol-induced G2-M arrest and apoptosis in human ovarian cancer cells grown as multicellular tumour spheroids*. Cancer Res 1997; 57:238893.
7. Levine B. *Cell biology: autophagy and cancer*. Nature 2007; 446:745-7.
8. Degenhardt K et al. *Autophagy promotes tumour cell survival and restricts necrosis, inflammation, and tumourigenesis*. Cancer Cell 2006; 10:51-64.
9. Karantza-Wadsworth V et al. *Autophagy mitigates metabolic stress and genome damage in mammary tumourigenesis*. Genes Dev 2007; 21:1621-35.
10. Mizushima N et al. *Autophagy fights disease through cellular selfdigestion*. Nature 2008; 451:1069-75.
11. Edinger A L and Thompson C B. *Death by design: apoptosis, necrosis and autophagy*. Curr Opin Cell Biol 2004; 16:663-9.
12. Herrmann R et al. *Screening for compounds that induce apoptosis of cancer cells grown as multicellular spheroids*. J Biomol Screen 2008; 13:1-8.
13. Hägg M et al. *A novel high-through-put assay for screening of pro-apoptotic drugs*. Invest New Drugs 2002; 20:253-9.
14. Friedrich J et al. *A reliable tool to determine cell viability in complex 3-d culture: the acid phosphatase assay*. J Biomol Screen 2007; 12:92537.
15. Schmidt-Mende J et al. *Early mitochondrial alterations in ATRA-induced cell death. Cell Death Differ* 2006; 13:119-28.
16. Lamb J et al. *The Connectivity Map: using gene-expression signatures to connect small molecules, genes, and disease*. Science 2006; 313:1929-35.
17. Linden T et al. *The antimycotic ciclopiroxolamine induces HIF-1alpha stability, VEGF expression, and angiogenesis*. FASEB J 2003; 17:761-3.
18. Yu Y et al. *Chelators at the cancer coalface: desferrioxamine to Triapine and beyond*. Clin Cancer Res 2006; 12:6876-83.
19. Klionsky D J et al. *Guidelines for the use and interpretation of assays for monitoring autophagy in higher eukaryotes*. Autophagy 2008; 4:151-75.
20. Amaravadi R K and Thompson C B. *The roles of therapy-induced autophagy and necrosis in cancer treatment*. Clin Cancer Res 2007; 13:7271-9.
21. Mazure N M and Pouyssegur J. *Hypoxia-induced autophagy: cell death or cell survival?* Curr Opin Cell Biol 2009.
22. Lum J J et al. *Growth factor regulation of autophagy and cell survival in the absence of apoptosis*. Cell 005; 120: 237-48.
23. Bruick R K. *Expression of the gene encoding the proapoptotic Nip3 protein is induced by hypoxia*. Proc Natl Acad Sci USA 2000; 97:9082-7.
24. Vande Velde C et al. *BNIP3 and genetic control of necrosis-like cell death through the mitochondrial permeability transition pore*. Mol Cell Biol 2000; 20:5454-68.
25. Tong W H and Rouault T A. *Metabolic regulation of citrate and iron by aconitases: role of iron-sulfur cluster biogenesis*. Biometals 2007; 20:549-64.
26. Arteel G E et al. *Reductive metabolism of the hypoxia marker pimonidazole is regulated by oxygen tension independent of the pyridine nucleotide redox state*. Eur J Biochem 1998; 253:743-50.
27. Corradetti M N et al. *Regulation of the TSC pathway by LKB1: evidence of a molecular link between tuberous sclerosis complex and Peutz-Jeghers syndrome*. Genes Dev 2004; 18:1533-8.
28. Schieke S M et al. *The mammalian target of rapamycin (mTOR) pathway regulates mitochondrial oxygen consumption and oxidative capacity*. J Biol Chem 2006; 281:27643-52.
29. Cunningham J T et al. *mTOR controls mitochondrial oxidative function through a YY1-PGC-1alpha transcriptional complex*. Nature 2007; 450:736-40.
30. Carracedo A and Pandolfi P P. *The PTEN-PI3K pathway: of feedbacks and cross-talks*. Oncogene 2008; 27:5527-41.
31. Sariban-Sohraby S and al. *Comparison of energy metabolism in human normal and neoplastic (Burkitt's lymphoma) lymphoid cells*. Cancer Res 1983; 43:4662-4.
32. Freyer J P et al. *In situ oxygen consumption rates of cells in V-79 multicellular spheroids during growth*. J Cell Physiol 1984; 118:53-61.
33. Kunz L A et al. *Oncogene-associated growth behavior and oxygenation of multicellular spheroids from rat embryo fibroblasts*. Adv Exp Med Biol 1994; 345:359-66.
34. Bredel-Geissler A et al. *Proliferation-associated oxygen consumption and morphology of tumour cells in monolayer and spheroid culture*. J Cell Physiol 1992; 153:44-52.
35. Finch R A et al. *Triapine (3-aminopyridine-2-carboxaldehyde-thiosemicarbazone): A potent inhibitor of ribonucleotide reductase activity with broad spectrum antitumour activity*. Biochem Pharmacol 2000; 59:983-91.

36. Torti S V et al. *Tumour cell cytotoxicity of a novel metal chelator*. Blood 1998; 92:1384-9.
37. Rakba N et al. *Antiproliferative and apoptotic effects of O-Trensox, a new synthetic iron chelator, on differentiated human hepatoma cell lines*. Carcinogenesis 2000; 21:943-51.
38. Richardson D R. *Iron chelators as therapeutic agents for the treatment of cancer*. Crit Rev Oncol Hematol 2002; 42:267-81.
39. Ohyashiki J H et al. *The oral iron chelator deferasirox represses signaling through the mTOR in myeloid leukemia cells by enhancing expression of REDD1*. Cancer Sci 2009; 100:970-7.
40. Wang H et al. *Dexamethasone represses signaling through the mammalian target of rapamycin in muscle cells by enhancing expression of REDD1*. J Biol Chem 2006; 281:39128-34.
41. Tracy K et al. *BNIP3 is an RB/E2F target gene required for hypoxia-induced autophagy*. Mol Cell Biol 2007; 27:6229-42.
42. Ramanathan A and Schreiber S L. *Direct control of mitochondrial function by mTOR*. Proc Natl Acad Sci USA. 2009; 106:22229-32
43. Degtyarev M et al. *Akt inhibition promotes autophagy and sensitizes PTEN-null tumours to lysosomotropic agents*. J Cell Biol 2008; 183:101-16.

What is claimed is:

1. A method for treating a solid cancer tumour in a person, comprising administering a pharmacologically cancer-combating effective dose of a compound of formula I:

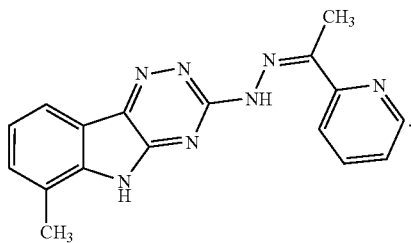

2. The method of claim 1, further comprising administering an autophagy inhibiting agent to the person.

3. The method of claim 2, wherein the autophagy inhibiting agent is chloroquine.

4. The method of claim 2, wherein the autophagy inhibiting agent is selected from the group consisting of hydroxychloroquine, 3-methyladenine, adenosine, bafilomycin A1, 5-amino-4-imidazole carboxamide riboside, wortmannin, and viniblastine.

5. The method of claim 1, wherein the compound of formula 1 is administered in a pharmaceutically suitable carrier.

6. The method of claim 1, wherein the compound is administered per-orally.

7. The method of claim 1, wherein the compound is administered parenterally.

8. The method of claim 1, wherein the compound is in the form of microparticles of a size of 10 µm or smaller.

9. A method for treating a solid colon cancer tumour in a person, comprising administering a pharmacologically cancer-combating effective dose of a cell permeable iron chelator of formula I:

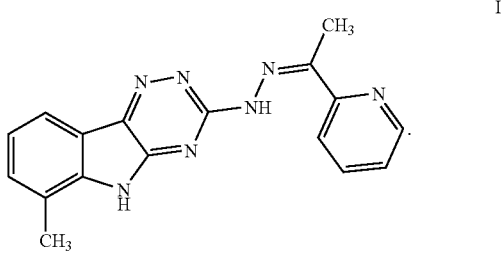 [SMILES: C/C(=N/Nc1nnc2c(n1)[nH]c1c(C)cccc12)c1ccccn1]

10. The method of claim 9, further comprising administering an autophagy inhibiting agent to the person.

11. The method of claim 10, wherein the autophagy inhibiting agent is chloroquine.

12. The method of claim 10, wherein the autophagy inhibiting agent is selected from the group consisting of hydroxychloroquine, 3-methyladenine, adenosine, bafilomycin A1, 5-amino-4-imidazole carboxamide riboside, wortmannin, and viniblastine.

13. The method of claim 9, wherein the compound of formula 1 is administered in a pharmaceutically suitable carrier.

14. The method of claim 9, wherein the compound is administered per-orally.

15. The method of claim 9, wherein the compound is administered parenterally.

16. The method of claim 9, wherein the compound is in the form of microparticles of a size of 10 µm or smaller.

* * * * *